US00PP34078P2

(12) United States Plant Patent
Masor

(10) Patent No.: US PP34,078 P2
(45) Date of Patent: Mar. 29, 2022

(54) COLEUS PLANT NAMED 'BALTAZRIP'

(50) Latin Name: *Plectranthus scutellarioides*
Varietal Denomination: Baltazrip

(71) Applicant: Ball Horticultural Company, West Chicago, IL (US)

(72) Inventor: Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/532,463

(22) Filed: Nov. 22, 2021

(51) Int. Cl.
*A01H 5/12* (2018.01)
*A01H 6/50* (2018.01)

(52) U.S. Cl.
USPC ..... Plt./373
CPC ..... *A01H 6/50* (2018.05)

(58) Field of Classification Search
USPC ..... Plt./373
CPC ..... A01H 6/50
See application file for complete search history.

(56) References Cited

PUBLICATIONS

North Carolina Extension, Northe Carolina Extension Gardener Plant Toolbox, Coleus *scutellarioides*, downloaded from https://plants.ces.ncsu.edu/plants/coleus-scutellarioides/ on Dec. 12, 2021.*

* cited by examiner

*Primary Examiner* — Anne Marie Grunberg
(74) *Attorney, Agent, or Firm* — Audrey Charles

(57) ABSTRACT

A new and distinct cultivar of *Coleus* plant named 'Baltazrip', characterized by its dark greyed-purple, medium red-purple, medium green, and white multicolored foliage, and moderately vigorous, spreading growth habit, is disclosed.

1 Drawing Sheet

Latin name of genus and species of plant claimed: *Plectranthus scutellarioides.*

Variety denomination: 'Baltazrip'.

BACKGROUND OF THE INVENTION

The present invention relates to a new and distinct cultivar of *Coleus* plant botanically known as *Plectranthus scutellarioides* and hereinafter referred to by the cultivar name 'Baltazrip'.

The new cultivar originated in a controlled breeding program in Guadalupe, Calif. during November 2017. The objective of the breeding program was the development of *Coleus* cultivars with unique foliage coloration and leaf shape, spreading growth habit, and good sun tolerance.

The new *Coleus* cultivar is the result of cross-pollination. The female (seed) parent of the new cultivar is Lava Rose 'Kakegawa CE1', U.S. Plant Pat. No. 15,370, characterized by its dark purple and medium green colored foliage, and moderately vigorous, spreading growth habit. The male (pollen) parent of the new cultivar is the proprietary *Plectranthus scutellarioides* breeding selection coded RS3286-7, not patented, characterized by its medium purple and dark pink colored foliage, and vigorous, spreading growth habit. The new cultivar was discovered and selected as a single flowering plant within the progeny of the above stated cross-pollination during April 2018 in a controlled environment in Cartago, Costa Rica.

Asexual reproduction of the new cultivar by terminal stem cuttings since April 2018 in Cartago, Costa Rica, Arroyo Grande, Calif. and West Chicago, Ill. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baltazrip' as a new and distinct cultivar of *Coleus* plant:

1. Dark greyed-purple, medium red-purple, medium green, and white multicolored foliage, and
2. Moderately vigorous, spreading growth habit.

Plants of the new cultivar differ from plants of the female parent primarily in having a different foliage color that includes areas of red-purple and white. Plants of the new cultivar differ from plants of the male parent primarily in having reduced growth vigor and a different foliage color that includes areas of green and white.

Of the many commercially available *Coleus* cultivars, the most similar in comparison to the new cultivar is GREAT FALLS Iguazu 'Docogrefalig', U.S. Plant Pat. No. 31,031. However, in comparison, plants of the new cultivar differ from plants of 'Docogrefalig' in at least the following characteristics:

1. Plants of the new cultivar have an upper leaf surface color having darker, green-colored margins than plants of 'Docogrefalig';
2. Plants of the new cultivar have a lower leaf surface color having dark and medium greyed-purple unlike the medium yellow green of plants of 'Docogrefalig'; and
3. Plants of the new cultivar have larger leaves than plants of 'Docogrefalig'.

BRIEF DESCRIPTION OF THE PHOTOGRAPHS

The accompanying photographs show, as nearly true as it is reasonably possible to make the same in color illustrations of this type, the overall growth habit and typical foliage characteristics of the new cultivar. Colors in the photographs differ slightly from the color values cited in the detailed description, which accurately describes the colors of 'Baltazrip'. The approximately 8-week-old plants were grown in 6-inch pots for 5 weeks in a greenhouse in West Chicago, Ill. Plants were given one pinch one week before transplant.

DETAILED BOTANICAL DESCRIPTION

Figure 1:
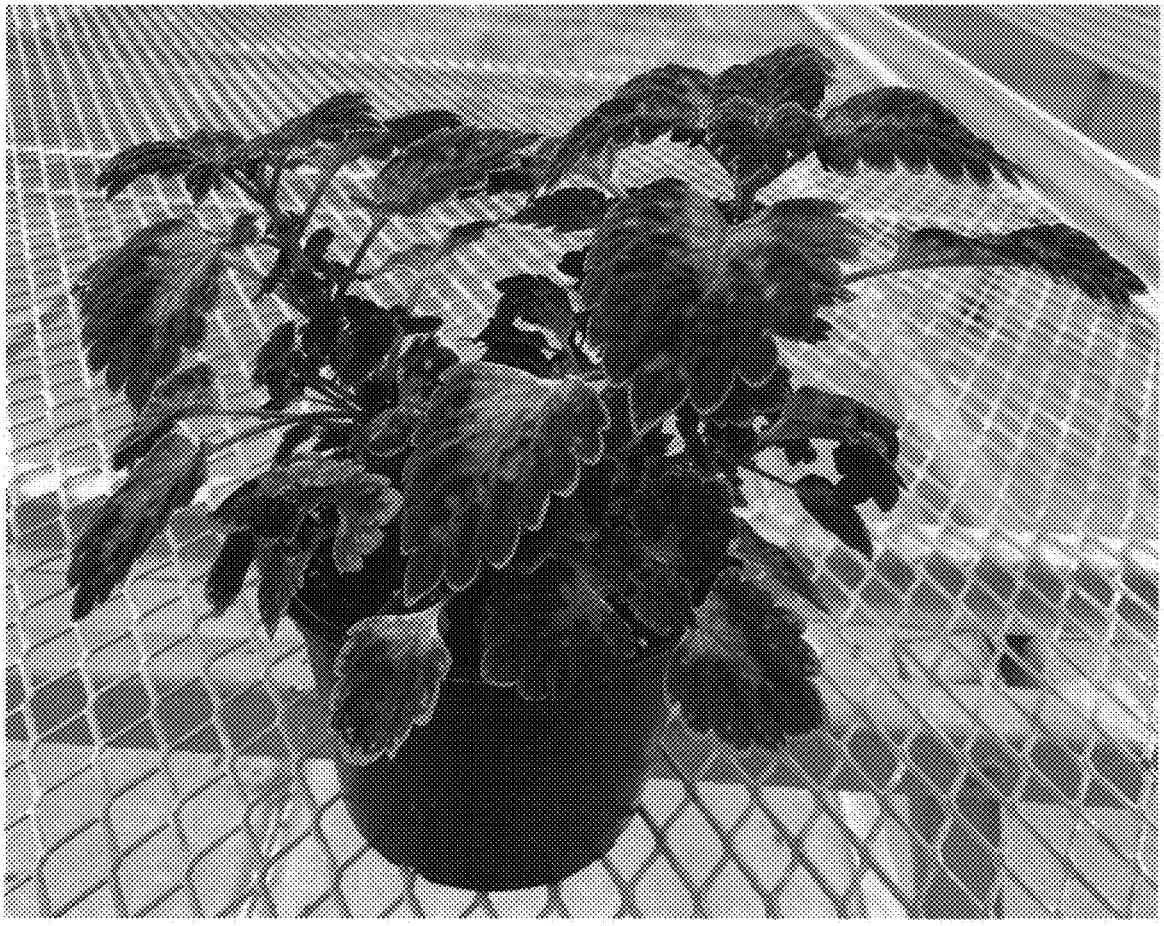
FIG. 1 illustrates a side view of the overall growth habit of 'Baltazrip'.
Figure 2:
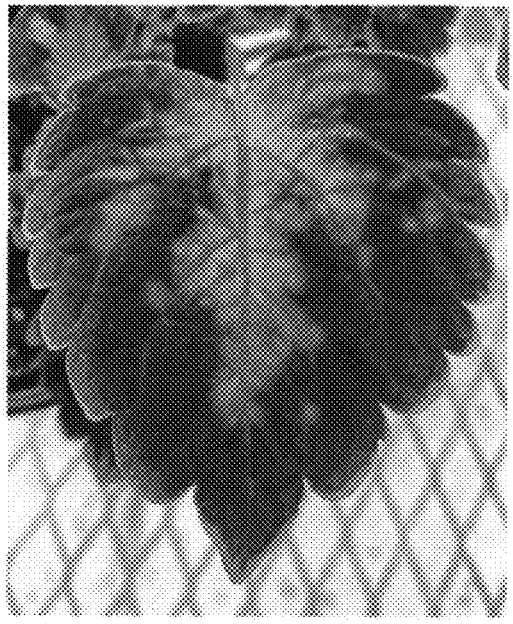
FIG. 2 illustrates a close-up view of an individual leaf of 'Baltazrip'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in November 2021 under natural light conditions in Naperville, Ill.

The following descriptions and measurements describe approximately 8-week-old plants produced from cuttings from stock plants and grown in a polycarbonate greenhouse under conditions comparable to those used in commercial practice. The plants were grown in West Chicago, Ill. in 6-inch pots for 5 weeks utilizing a soilless growth medium. Plants were given one pinch one week before transplant. Greenhouse temperatures were maintained at approximately 67° F. to 71° F. (19° C. to 22° C.) during the day and approximately 65° F. to 70° F. (18° C. to 21° C.) during the night. Supplemental lighting was used. Measurements and numerical values represent averages of typical plants.

Botanical classification: *Plectranthus scutellarioides* 'Baltazrip'.

Parentage:

*Female parent.*—Lava Rose, 'Kakegawa CE1', U.S. Plant Pat. No. 15,370.

*Male parent.*—Proprietary *Plectranthus scutellarioides* breeding line coded RS3286-7, not patented.

Propagation:

*Type cutting.*—Terminal stem.

*Time to initiate roots.*—Approximately 4 to 6 days.

*Time to produce a rooted cutting.*—Approximately 14 to 21 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, spreading.

*Size.*—Height from soil level to top of plant plane: Approximately 15.0 cm. Width: Approximately 39.0 cm.

*Branching habit.*—Freely branching, pinching not required but improves basal branching. Quantity of lateral branches per plant: Approximately 2 branches each with approximately 4 lateral branches.

*Branch.*—Strength: Moderately strong. Shape: Square with rounded edges in cross section. Length: Approximately 15.5 cm. Diameter at central internode: Approximately 6.0 mm. Length of central internode: Approximately 2.5 cm. Texture: Dense minute pubescence. Color of young and mature stems: 146B with a faint tint of 187A.

Foliage description:

*General description.*—Quantity of leaves per main branch: Approximately 12. Fragrance: None. Form: Simple. Arrangement: Opposite.

*Leaves.*—Aspect: Petiole is at an acute angle to stem; leaf blade is perpendicular to stem, and transitions to an obtuse angle with age. Appearance: Matte. Shape: Deltoid. Margin: Deeply crenate. Apex: Acute. Base: Truncate. Venation pattern: Pinnate. Length of mature leaf: Approximately 7.0 cm. Width of mature leaf: Approximately 6.0 cm. Texture of upper surface: Sparsely pubescent. Texture of lower surface: Sparsely pubescent with densely pubescent venation, venation raised. Color of upper surface of young and mature foliage: Closest to but darker than 187A with irregular centers and spotting of closest to 71A to 71C, lobed portion of margins of 137A, small irregular patches of 155A at base; venation of 187D or indistinguishable from leaf lamina. Color of lower surface of young and mature foliage: Closest to 187A with irregular centers of closest to 186A to 186C, and venation closest to 196B or indistinguishable from leaf lamina.

*Petiole.*—Length: Approximately 4.0 cm to 5.0 cm. Width: Approximately 3.0 mm. Texture: Densely pubescent. Color: 146B to 146A lightly tinted with N186A.

Flowering description: To date, flower development has not been observed on plants of the new *Coleus*.

Disease and pest resistance: To date, resistance to pathogens and pests common to *Coleus* has not been observed.

What is claimed is:

1. A new and distinct cultivar of *Coleus* plant named 'Baltazrip', substantially as herein illustrated and described.

* * * * *